(12) United States Patent
Amirav et al.

(10) Patent No.: US 11,129,947 B2
(45) Date of Patent: *Sep. 28, 2021

(54) MASK FOR ADMINISTRATION OF INHALED MEDICATION

(71) Applicant: Nostrum Technology LLC, New Brunswick, NJ (US)

(72) Inventors: Israel Amirav, Rosh Pina (IL); Asaf Halamish, Pardes Hana-Karkur (IL); Michael Newhouse, Hamilton (CA); K. Mosaddeq Hossain, Hillsborough, NJ (US); Paresh Vasandani, Somerset, NJ (US); Vijay Shukla, Highland Park, NJ (US)

(73) Assignee: NOSTRUM TECHNOLOGY LLC, Somerset, NJ (US)

( * ) Notice: Subject to any disclaimer, the term of this patent is extended or adjusted under 35 U.S.C. 154(b) by 52 days.

This patent is subject to a terminal disclaimer.

(21) Appl. No.: 16/423,728

(22) Filed: May 28, 2019

(65) Prior Publication Data
US 2019/0275266 A1 Sep. 12, 2019

Related U.S. Application Data

(63) Continuation of application No. 13/494,458, filed on Jun. 12, 2012, now abandoned.
(Continued)

(51) Int. Cl.
*A61M 15/00* (2006.01)
*A61M 16/06* (2006.01)
(Continued)

(52) U.S. Cl.
CPC .......... *A61M 15/00* (2013.01); *A61J 17/1011* (2020.05); *A61M 15/0018* (2014.02);
(Continued)

(58) Field of Classification Search
CPC .. A61M 15/00; A61M 15/0018; A61M 16/06; A61M 11/00; A61M 2016/0661;
(Continued)

(56) References Cited

U.S. PATENT DOCUMENTS

| 1,395,948 A | 11/1921 | Drager |
| 4,809,692 A | 3/1989 | Nowacki et al. |

(Continued)

FOREIGN PATENT DOCUMENTS

| WO | 2010076715 A1 | 7/2010 |
| WO | 20110125061 A1 | 10/2011 |

OTHER PUBLICATIONS

Canadian Office Action issued in corresponding Canadian Patent Application No. 2,853,506, dated Apr. 20, 2018.
(Continued)

*Primary Examiner* — Kendra D Carter
*Assistant Examiner* — Jonathan S Paciorek
(74) *Attorney, Agent, or Firm* — Greenberg Traurig, LLP; Jonathan D. Ball; Tanzina Chowdhury

(57) ABSTRACT

A breathing mask for use in administering inhalable medications to a patient in need of an inhaled drug is provided. The mask disclosed herein is particularly useful for use with very young children. The mask is made from a flexible molded plastic silicone or elastomeric material, and has an anthropometrically/anatomically/ergonomically contoured shape to provide a good seal, a comfortable fit, and minimal dead space within the mask. The airway is aligned with nose. There may be an orifice for use with a soother device to calm a child using the mask. Also provided is a visual flow indicator to provide an indication of the quality of the seal of the mask on the face.

26 Claims, 3 Drawing Sheets

Related U.S. Application Data

(60) Provisional application No. 61/498,384, filed on Jun. 17, 2011.

(51) Int. Cl.
*A61J 17/00* (2006.01)
*A61M 11/00* (2006.01)

(52) U.S. Cl.
CPC ............ *A61M 16/06* (2013.01); *A61J 17/001* (2015.05); *A61M 11/00* (2013.01); *A61M 2016/0661* (2013.01); *A61M 2205/13* (2013.01); *A61M 2205/583* (2013.01); *A61M 2205/59* (2013.01); *A61M 2240/00* (2013.01)

(58) Field of Classification Search
CPC ........ A61M 2205/13; A61M 2205/583; A61M 2205/59; A61M 2240/00; A61J 17/1011; A61J 17/001
See application file for complete search history.

(56) References Cited

U.S. PATENT DOCUMENTS

| | | | |
|---|---|---|---|
| 4,832,015 A * | 5/1989 | Nowacki | A61M 15/0016 128/205.23 |
| 5,012,803 A | 5/1991 | Foley et al. | |
| 5,012,804 A | 5/1991 | Foley et al. | |
| 5,375,593 A | 12/1994 | Press | |
| 5,462,050 A | 10/1995 | Dahlstrand | |
| 5,462,852 A | 10/1995 | Dahlstrand | |
| 5,535,741 A | 7/1996 | Widerström et al. | |
| 5,560,354 A | 10/1996 | Berthon-Jones et al. | |
| 5,645,049 A | 7/1997 | Foley et al. | |
| 5,738,094 A * | 4/1998 | Hoftman | A61M 16/06 128/206.24 |
| 5,846,082 A * | 12/1998 | Thornton | A61F 5/566 433/215 |
| 5,918,598 A | 7/1999 | Befler et al. | |
| 5,937,852 A | 8/1999 | Butler et al. | |
| 5,988,160 A | 11/1999 | Foley et al. | |
| 6,405,729 B1 | 6/2002 | Thornton | |
| 6,418,929 B1 | 7/2002 | Norfleet | |
| 64,700,882 | 10/2002 | Newhouse | |
| 6,571,798 B1 * | 6/2003 | Thornton | A61M 16/06 128/206.21 |
| 6,626,168 B1 | 9/2003 | Carroll et al. | |
| 6,904,908 B2 | 6/2005 | Bruce et al. | |
| 6,916,223 B2 | 7/2005 | Gallitognotta et al. | |
| 7,004,162 B1 * | 2/2006 | Foley | A61M 15/00 128/200.14 |
| 7,201,165 B2 | 4/2007 | Bruce et al. | |
| 2003/0037788 A1 | 2/2003 | Gallem | |
| 2007/0006879 A1 | 1/2007 | Thorton | |
| 2008/0006274 A1 * | 1/2008 | Thornton | A61M 16/06 128/206.21 |
| 2008/0006276 A1 * | 1/2008 | Kreutzmann | A61M 16/0616 128/206.24 |
| 2008/0110463 A1 | 5/2008 | Hajgato et al. | |

OTHER PUBLICATIONS

Supplementary European Search Report issued in Application No. EP 12 8 0045, dated Oct. 21, 2014.
Examination Report No. 2 for standard patent application issued in Australian Patent Application No. 2012271836, dated Dec. 13, 2016.
International Search Report dated Sep. 12, 2012 for International Application No. PCT/US2012/042055.
English Translation of Rejection to Grant in corresponding Mexican Patent Application No. MX/a2013/015004, dated Dec. 17, 2020 (13 pages).
Communication pursuant to Article 94(3) EPC issued in European Application No. 12 800 042.2 dated Sep. 28, 2017.
Examination Report No. 1 for standard patent application issued in Australian Patent Application No. 2012271836, dated Jan. 29, 2016.

* cited by examiner

MASK FOR ADMINISTRATION OF INHALED MEDICATION

CROSS REFERENCE TO RELATED APPLICATION

This application claims priority to U.S. patent application Ser. No. 13/494,458 filed on Jun. 12, 2012 which claims priority to U.S. provisional patent application No. 61/498,384, filed Jun. 17, 2011, the entire contents of which are incorporated herein by reference.

FIELD OF THE INVENTION

The present invention relates to a mask for the administration of inhalable drugs, particularly by children and infants.

BACKGROUND

A significant problem faced by medical professionals is the need for effective devices for the delivery of drugs to infants and children, in particular inhalable drugs in the form of aerosols, powders, vapors, or mists. Typical examples of such drugs that are widely used are asthma drugs, which employ pressurized metered dose inhalers (MDI) that deliver a measured dose of an aerosolized liquid or powder to a mouthpiece. In some cases, holding chambers are used, that serve to trap larger particles and provide a reservoir for suspended drug aerosol if the chamber is used with an inhalation mask. Other devices such as nebulizers are also in common use, and other diseases besides asthma are treatable by inhaled drugs. Most adults can simply use a mouthpiece in a device that administers an inhalable drug, and can coordinate their breathing with the use of an MDI or the flow of an inhalable drug. Children however lack the coordination, understanding, or communication skills necessary to use conventional drug inhalation devices. Accordingly, the use of an inhalation mask is required for children.

Breathing masks for use with children have several special requirements. The masks must be sized appropriately for children's' faces, which is not necessarily a matter of merely shrinking an adult-sized mask. The size and shape of the mask are critical to providing a good seal at the edges of the mask, to prevent leakage of medication to the eyes, and also to prevent loss of dose that would otherwise go to the lungs. Additionally, maintaining eye contact with the child may be important with young children, so a suitable mask should not cover the eyes or obscure vision. Also, a known problem with infants or children in the administration of inhaled medicaments is that existing masks often cause agitation and distress in a child, and makes them cry. If this occurs, the child will usually become uncooperative, and the disruption and uneven breathing during crying will probably prevent effective delivery of the drug substance to the lungs.

An approach to the problem of agitation caused by a mask, as previously disclosed by the instant inventors in U.S. Pat. No. 6,470,882, is the use of "soother device" in the mask for small children. A soother device is defined as a something the child can suck on, which has a calming effect. As set forth in U.S. Pat. No. 6,470,882, soother devices can be a "pacifier," that is a plastic nipple that infants suck on, a bottle with a nipple, or a natural mothers breast. This concept takes advantage of the fact that small children, up to about age 18 months, are obligate nasal breathers, and infants are easily capable sucking from the breast or bottle without interrupting normal breathing. As disclosed in U.S. Pat. No. 6,470,882, a soother device inserted into the mouth section of an inhalation mask, covering the mouth and nose of an infant, can comfort a small child.

Another problem with infants and children in the administration of inhaled medicaments is that masks for children have hitherto been essentially shrunken versions of masks used for the administration of oxygen or anesthesia in adults. These prior art masks are sub-optimal. They tend to not fit well, tend not to have a good seal, and often fit poorly at the extremes in size, so a plurality of sizes is necessary to ensure a good fit. Another significant consideration is that children's faces change rapidly in the first few years of life, so a mask that is effective at say, 12 months of age may not provide a good seal at 18 months of age. Furthermore, most currently available masks have the airway for delivery of medication flow aligned with the mouth, and this design is used on most prior art children's medication masks based on adult mask designs. As noted elsewhere herein, infants are nasal breathers, so this alignment assures substantial (and undesirable) dead space in the mask.

Minimization of dead space is a desirable feature in a medication mask. Dead space is not a substantial problem with oxygen therapy or inhaled anesthesia, because the active gas for oxygen therapy or anesthesia is the fraction of active gas as a volume or partial pressure percentage of the active gas in ordinary air. The active gas can be used in excess at minimal cost, and metering of an absolute quantity of active substance is generally not important.

By contrast, with inhaled therapies for respiratory diseases, such as asthma, cystic fibrosis, bronchitis, etc., or for inhaled drugs for other conditions that are intended for deliver to the lungs, the absolute dose of the active drug usually is important. A certain quantity of medication is placed into the device, and the medical objective is to have as much of the medication inhaled into the lungs as possible. If there is a large dead space, a substantial amount of the active drug may be suspended in the dead space after an initial inhalation. That quantity of drug will be largely expelled from the dead space on the exhalation cycle, because all masks require an exhalation valve to vent exhaled air. With a small dead space, there is less volume for drug to remain suspended within the mask, so a greater percentage of the total dose will be inhaled, and a smaller quantity of drug will be expelled from the device on the exhalation.

In the administration of inhaled drugs, essentially two types of devices are in common use, nebulizers and metered dose inhalers (MDI's). Nebulizers have a reservoir containing a drug solution through which a stream of air is bubbled through or over (typically). The air stream generates a mist or vapor, of atomized droplets suspended in air, which is conveyed to the mouth of the patient through a tube and a mouthpiece. In the case of invalid adults or small children up to the age of about 5 years, a mask is used.

MDI's are used for a wide variety of inhaled drugs, for example β-agonists, steroids, and anticholinergic drugs, for use in asthma, bronchitis, COPD and other respiratory ailments. MDI's typically comprise a canister with a metering device and exhaust nipple. The canister contains a solution or suspension of a drug under pressure. A plastic actuator holds the canister and has a mouthpiece. Depressing the canister in the actuator actuates the delivery of a dose. Adults and older children can use the mouthpiece on the actuator directly, by coordinating their breathing with actuation.

In many cases, MDI's are used with a holding chamber or spacer, which is typically a tube about 10 cm long and 5 cm in diameter, that has a receptacle at the rear for holding an MDI, and a mouthpiece at the front end. The drug is introduced into the chamber, and then inhaled by the patient from the mouthpiece. Compared to an MDI without a chamber, the chamber is usually used to trap large particles that would otherwise lodge in the mouth or throat, causing irritation, rather than enter the lungs, which is the intended target organ. Additionally, the use of a spacer reduces or eliminates the need for the patient to coordinate their breathing with the actuation, since the drug can remain suspended in the chamber for several seconds until the patient inhales it.

MDI chambers can also be coupled to a breathing mask for use by patients who cannot use a mouthpiece, such as small children or incompetent patients. A caregiver actuates the MDI and the suspended drug substance enters the chamber and is then inhaled by the patient with no need to coordinate breathing or use of a mouthpiece. A suitable mask typically will have an inhalation valve and an exhalation valve. The inhalation valve is one-way, only allowing air to travel from the chamber into the mask, so that air with suspended drug is only drawn through the chamber during inhalation. The inhalation valve blocks exhaled air from entering the chamber and blowing drug out the back end vents. The exhalation valve is a one-way valve that allows exhaled air to vent out of the interior of the mask, but does not allow outside air to enter during inhalation. An example of a chamber and mask for use with an MDI is disclosed in U.S. Pat. No. 6,904,908.

As noted above, the fit of a mask is critical for maintaining a good seal. But, there is little empirical or scientific evidence for the design of pediatric masks for use in children. The issue of adequate fit is a particular problem in infants and young children whose face undergoes rapid and marked developmental change in the first few years of life. The lack of scientific evidence to support existing face mask design in this age group explains why infant/toddler facemask design is suboptimal, particularly with regard to aerosol delivery where a tight seal is important in order to prevent leakage of drugs such as aerosolized corticosteroids, towards the eyes. A tightly fitting mask is also necessary to minimizing potentially sensitizing agents, such as antibiotics, from leaking into the caregivers' environment.

SUMMARY OF THE INVENTION

This invention provides a mask for administering an inhalable medication to a patient. The mask may employ a flexible ergonomically shaped molded elastomeric face mask body covering the nose and mouth of the patient. The body of the mask includes a nose section and a mouth section. The edge of the mask in contact with the patient's face is a thin soft lip that may be angled outward from the interior of the mask. The drug delivery path is aligned with the nose of the patient. The mask has an ergonomically contoured mouth section shaped to fit close to the mouth and lips of the patient with minimal dead space in the mouth section.

In an embodiment, the mask is intended for use with infants or small children. In an embodiment, the mask has a soother device orifice in the mouth section of the mask. In another embodiment, the mask has a visual seal indicator that functions as a biofeedback device to indicate a secure seal.

DETAILED DESCRIPTION

Figure 1:
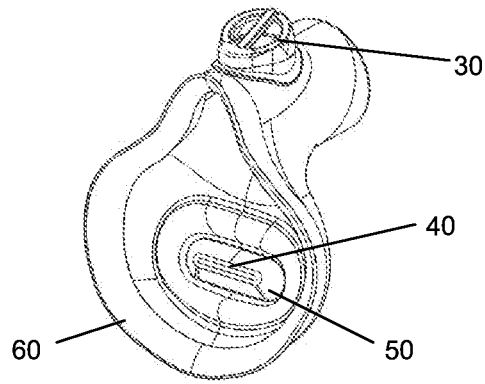
FIG. 1 is a perspective view of the rear of the small mask with a soother device orifice.

As used herein, the term "mask" refers to a flexible molded elastomeric body that covers the nose and mouth of a patient in need of an inhalable medication, and wherein the mask channels inhalable medication to the nose of the patient. The term "soother device" is a device intended to be sucked on in the mouth of an infant or small child. The term "anterior" refers the direction or face of the apparatus in the direction of the face of the patient. The term "posterior" is the direction or face facing away from the patient.

In an embodiment of the invention disclosed herein, a mask for administering an inhalable medication to a patient, with a flexible ergonomically shaped molded elastomer face mask body covering the nose and mouth of the patient, comprising a nose section and a mouth section, wherein the edge of the mask in contact with the patient's face is a thin soft lip; wherein the edge of the mask in contact with the face is contoured with at least one inflection point of at least approximately 10°; a drug delivery path aligned with the nose of the patient comprising an opening for receiving an inhalable medication in the nose section of the mask configured to minimize the dead space in the mask; and an ergonomically contoured mouth section shaped to fit close to the mouth and lips of the patient with minimal dead space in the mouth section.

In an embodiment, this invention further provides a method of administering an inhalable medicament to a patient using the mask disclosed in the preceding paragraph.

This invention provides novel inhalation mask designs for the administration of inhalable medications, with an ergonomically shaped and contoured shape, designed to fit close to the face, with minimal dead space, and an airway for receiving an inhalable medication aligned with the nose. In optional embodiments, there may be a visual indicator to assess the quality and effectiveness of the seal of the mask on the patient. In another embodiment, an orifice is provided for a soother device for use with small children.

In an embodiment, the ergonomically shaped and contoured face masks of this invention are specifically intended for use with infants or young children as patients in need of an inhalable medication. When used by a young child, these masks are intended for use with the assistance of an adult caregiver, such as a parent or medical assistant, who assists the child in using the mask and administering the inhalable medication with the inhalation masks of this invention. In embodiments intended for use with infants or young children as patients, the mask has an orifice for use with a soother device, such as a pacifier, that can relax the child while the mask is in use. In another embodiment, the mask has a cuttable section making the use of a soother device optional.

The inventive mask design features an airway in communication with a source of inhalable medication aligned with the nose, rather than the mouth, which is typical in prior art inhalation masks. The nasal alignment is generally useful for all patients, because nasal breathing is normally a preferred mode of breathing. In particular, children up to about 18 months of age are obligate nasal breathers, and older children also normally prefer to breathe through their nose. Additionally, the mask has a contoured shape, shaped to fit closely to the face. The ventral surface (e.g., 44 in FIG. 4) of the mouth section is contoured to conform to the shape of the face minimizing dead space in the interior of the mask. The combination of the airway configuration and the contoured profile of the instant masks substantially reduces the dead space within the mask, which is a highly desirable feature.

The instant masks may be used, for example, for administration of inhalable medication, such as inhaled gases, powders, mists, sprays, aerosols, or suspensions. These inhalable medications may be administered for example, from a metered dose inhaler (MDI) coupled to a holding chamber. In another embodiment, the instant masks are useful with a nebulizer.

In an embodiment, this invention provides a breathing face mask for administering inhaled medications to a patient, who may be a young child, age newborn to about five years old. The mask body comprises a molded elastomeric soft and flexible plastic material. The face mask covers the nose and mouth of the patient, and includes a nose section and a mouth section. The edge of the mask in contact with the patient's face is a thin soft lip that may be angled outward from the interior of the mask. The mask is shaped such that the edge in contact with the face is contoured with at least one inflection point of at least approximately 10°. In an embodiment, there are three or more such inflection points. The ventral surface of the mask over the mouth section is contoured to conform to the profile of a human face and minimize dead space in the interior of the mask.

The mask further has a drug delivery path aligned with the nose of the patient comprising an opening for receiving an inhalable medication in the nose section of the mask configured to minimize the dead space in the mask.

In an embodiment, there may be an orifice 40 in the mouth section 14 within which a soother device can be inserted. In alternative embodiments, there may be a thin section 42 of the ventral surface of the mask in the mouth section that is manufactured without an orifice for a soother device, but wherein the end user can easily cut or punch a hole in the thinned section to insert a soother device. In an embodiment, the ventral face of the mask in the mouth section is smooth for use with no soother device.

In an embodiment, the mask may have an exhalation valve 30 and a flow indicator mounted adjacent to the nostrils of the patient, providing a visual indication of exhalation by the patient. An embodiment of an exhalation valve 30 and a flow indicator is shown in FIG. 1. The visual indication may be a colored flap that moves in response to the breathing of the patient. The position of the flap can be viewed by a caregiver to confirm the exhalation of a patient, such as an infant or small child.

An important feature of a visual indicator is the indication of the quality of the seal of the mask on the face of the patient. The exhalation valve may comprise a biofeedback system, wherein the flow indicator moves in response to the exhalation by the patient thereby providing a visual indication of the quality of the seal around the face of the patient. Thus, if the seal of the mask around the face is poor, entrained room air may enter during inhalation or may exit during exhalation; or air may pass in either direction in between breaths of the patient. Such leakage of air around the edge of the mask is undesirable. It can lead, for example, to loss of medication, inefficient inhalation of medication, or eye irritation from medication leaking out of the mask into the eyes. Furthermore, any leakage increases the effective dead space in the mask, which is also undesirable. Any drug suspended in dead space at the end of an inhalation will likely be expelled, and lost to the environment, during exhalation. In the administration of drugs (as opposed to anesthesia), loss of drug is generally undesirable. The biofeedback from a visual indicator in the mask informs the caregiver that the seal is not optimal, suggesting that the mask needs to be repositioned on the face of the child.

In the embodiment with a soother device orifice, the orifice may comprise a duck-bill-type of structure, with the duck-bill pointed inward (toward the face of the patient). With this orifice, a soother device must be inserted prior to use. If present, the soother device orifice provides an effective seal to minimizes air leakage when a soother device is inserted.

The inventive masks, as shown in FIGS. 1-12, have an anthropometrically designed shape that is ergonomically contoured to fit the faces of patients, particularly that of infants or small children. The inventive masks are intended to fit snugly yet comfortably on the face of such patients.

The design of the child masks disclosed herein is the result of an extensive study by the instant inventors (to be published in full elsewhere) of the faces of approximately 350 children aged 2 to 55 months. This study was necessitated by an apparent lack of relevant data on facial dimensions in small children. The objective of the inventors' facial study was to design a mask so that the alignment and seal between the facial surface contours of small children and the mask are quantifiably optimized. That is, the mask should be designed to fit the specific population of infants and children by evaluating anthropometric data obtained from an appropriate population so that the mask fit is, on average, optimized and the number of mask sizes required is minimized in order to simplify prescribing for optimum fit.

Figure 13:
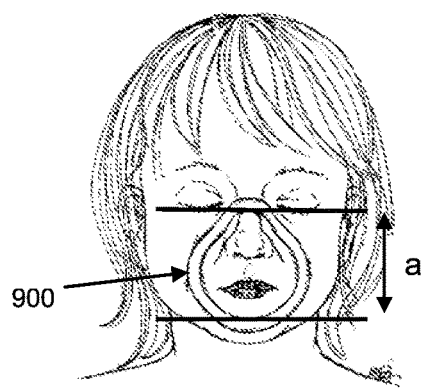
FIG. 13 is a schematic of the face of a child showing the area needing to be covered by an inhalation mask.

In the child facial study, various facial dimensions were anthropometrically measured with respect to the outline marked 900 in FIG. 13, including the dimension "a." Dimension "a" is the distance from a midpoint of the nose between the bridge and tip of the nose to the midpoint of the chin, which would be where a breathing mask would normally fit on a person's face. Facial dimensions in children were measured by two techniques. In one method, attempts were made to simply use a ruler placed on a child's face, take a photo, and record the measurements. This data proved to be difficult to obtain, because many children were not cooperative, and faces are soft and pliable, so changing facial expressions or crying distorts the facial surface anatomy, thus temporarily changing the dimensions. Overall, the results of measuring faces with a ruler were deemed to be fairly subjective and of limited value, so a different method was developed.

The other method of measuring faces was a 3-D topographic measurement method (anthropometric) developed in cooperation with the Technion University (Israel) Computer Science Department. The system is based on structured light technology where specially designed light patterns are projected on an object to obtain 3-D geometric model. This procedure worked well with infants and small children, producing 3-D maps of children's faces. Measurements with sub-millimeter accuracy that could be obtained quickly and easily, with minimal discomfort to the subjects.

In both the ruler and 3D methods, the distance in mm from the bridge of the nose to the lower edge of the upper lip, and the distance in mm from the upper edge of the lower lip to the protruding chin were measured. The two measurements for each subject were summed to get a "facial height" dimension.

An analysis of the data suggested that three mask sizes could be employed to effectively fit any child from birth to about 60 months of age. The approximate dimensions are shown in table 1. The height dimension in Table 1 corresponds to dimension "a" in FIG. 10.

TABLE 1

Dimensions of Masks

| Size | Height (inside dimension, in mm) |
| --- | --- |
| Small | 45 |
| Medium | 55 |
| Large | 64 |

The face study additionally gave the inventors facial contour parameters used to design the contour of the masks to maximize fit, comfort on the face, and a tight seal around the edges, while minimizing dead space in the mask.

The inventive masks, shown in FIGS. 1-12, have a body 10 fabricated from a flexible molded elastomeric material, such as a flexible silicone plastic. The masks have a nasal section 12 and a mouth section 14. The airway 20 is part of the nasal section. The lip 60 of the mask provides a seal around the face of the patient. In an embodiment, illustrated in FIGS. 1, 2, 9, and 10, a soother device orifice 40 is within the mouth section 14. The orifice 40 is also embedded in a flexible accordion region 50. The mask may also include an exhalation valve 30 and a visual seal indicator, which includes an indicator flap 32. In another embodiment, illustrated in FIGS. 3 and 5-8, the mask includes a thin section 42 that may be cut or punctured to insert a soother device such as a pacifier.

Figure 2:
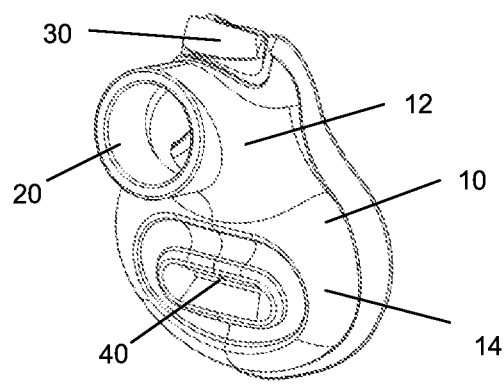
FIG. 2 is a perspective view of the front of the small mask with a soother device orifice.
Figure 3:
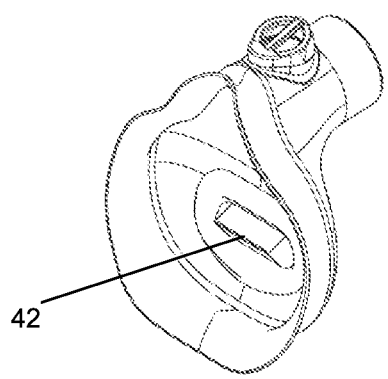
FIG. 3 is a perspective view of the rear of the small mask with the optional soother device design.
Figure 4:
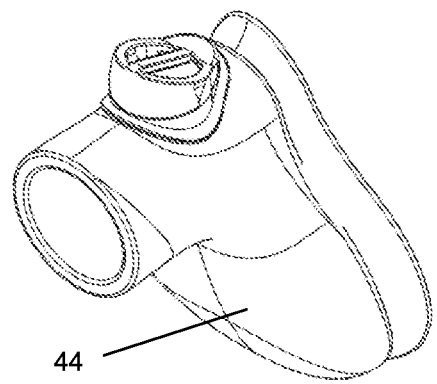
FIG. 4 is a perspective view of the front of the small mask with no soother orifice.
Figure 5:
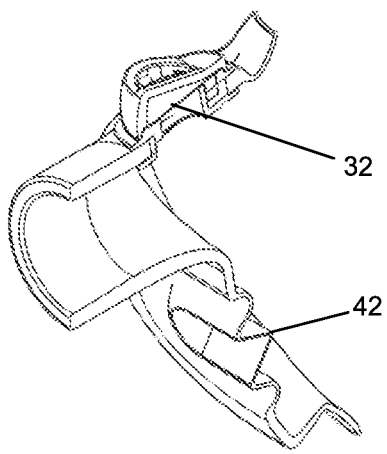
FIG. 5 is a cross-section view of the small mask with optional soother device design.
Figure 6:
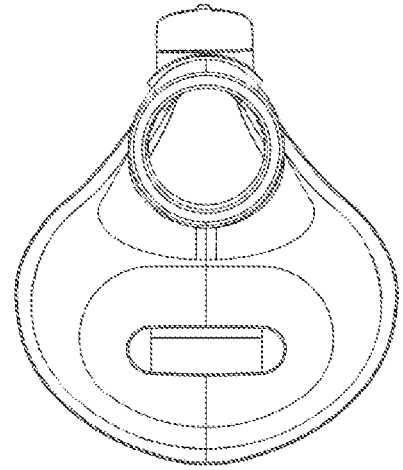
FIG. 6 is a front elevation view of the small mask with the optional soother device design.
Figure 7:
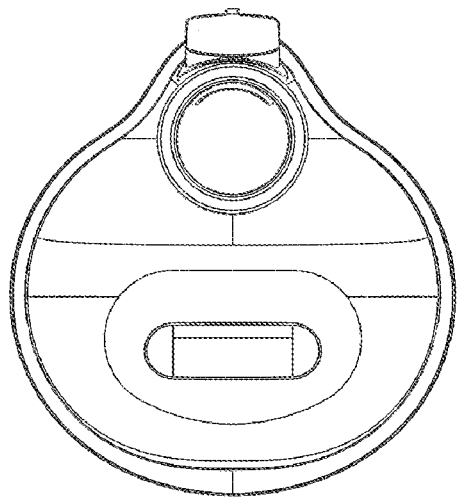
FIG. 7 is a front elevation of the medium mask with the optional soother device design.
Figure 8:
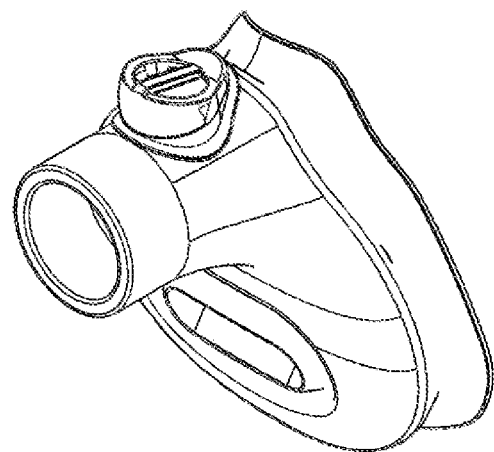
FIG. 8 is a perspective view of the front of the medium mask with the optional soother device design.
Figure 9:
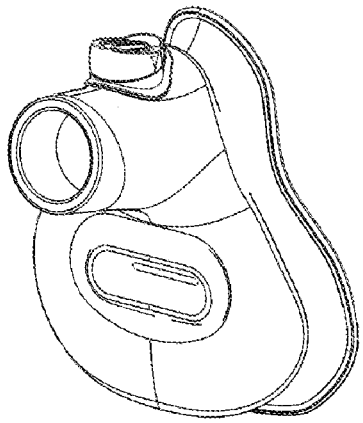
FIG. 9 is a perspective view of the front of the large mask with the optional soother device design.

FIGS. 1-6 show views of the small mask design from table 1. FIGS. 1 and 3 are a perspective views showing the interior of the small mask, that is, the side of the mask facing the patient. FIG. 2 is a perspective showing the exterior of the small mask, that is, the side facing away from the patient. FIG. 1 shows the small mask with a soother device orifice 40. FIG. 3 shows the soother device with a thin section 42 that may be an optional cuttable section. FIG. 5 is a cross section of the small mask, as if sliced vertically down the middle. FIG. 6 is a front elevation of the small mask.

Figure 10:
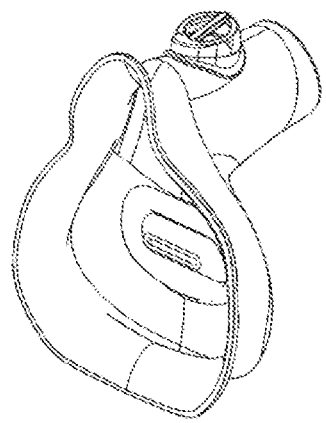
FIG. 10 is a perspective view of the rear of the large mask with the optional soother device design.
Figure 11:
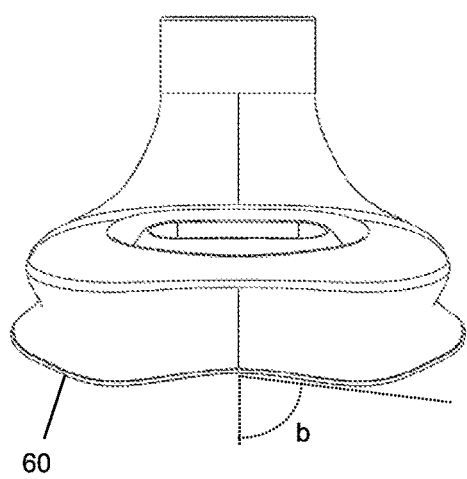
FIG. 11 is a bottom elevation of the medium mask.
Figure 12:
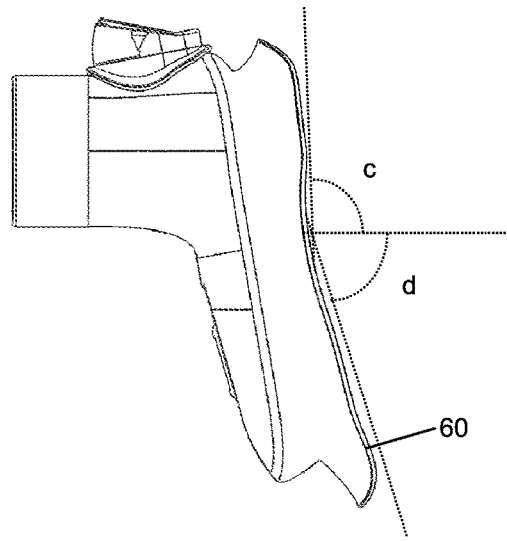
FIG. 12 is a left side elevation of the medium mask.

An embodiment of a medium size mask is shown in FIGS. 7, 8, 11, and 12. FIG. 11 is a bottom elevation of the medium mask, and FIG. 12 is a side elevation of the medium mask. FIGS. 10 and 11 show perspective views of the large size mask.

In one aspect, the inventive masks align the airway 20 with the nose. This substantially reduces the dead space in the mask and allows the face of the mask in front of the nose to be used as a position to insert a soother device.

In another aspect, the mask has a contoured edge 60, with at least one inflection point with an angle of 10° or more. These are the angles 90-b, 90-c, and 90-d in FIGS. 11 and 12. In fact, there are several such inflection points in the instant mask designs. Thus, angle b is on the bottom that fits over the chin. Angles c and d are on each side covering the cheek area of the face.

The facial study also provided data for the design of the body 10 of the mask, by providing scientific and quantified topographic facial dimensions. The 3D design conforms to the contour of the edges to maximize the fit and seal, and minimize the interior dead space of the mask. Ventral face 44 shown most clearly in FIG. 4 over the mouth section of the mask, is contoured according to these requirements to fit closely to the profile if a human face, minimizing the dead space in the mask. Thus, the inventive masks fit tightly yet comfortably to the face. The patient is not burdened with a large uncomfortable plastic object on their face, but rather a much smaller and comfortable device.

In an additional aspect, the inventive masks have a lip 60 comprising a soft, pliable plastic silicone or other elastomer material. In an embodiment (as shown in the drawings), the lip may be angled outward, away from the interior of the mask. An outward orientation of the lip helps to minimize the interior dead space of the mask, and contributes to the comfort of the fit and to the seal of the mask. In an embodiment, the inventive mask may be fabricated as a unitary molded plastic article, so the edge region of the mask in contact with skin and forming a seal will be a thinner (i.e., less thick) region of the mask, compared to the main body of the mask.

In embodiments with a soother device orifice 40, a soother device such as a pacifier must be inserted into the orifice prior to use of the mask. Here, the flexible flaps of the duckbill orifice make a good seal around the nipple of the pacifier minimizing air leakage at the soother device orifice. For example, the child's own pacifier may be used, which is simply inserted into the orifice 40, so the child is most comfortable with her/his own pacifier.

When a pacifier is used, the sucking action in the pacifier connected to the mask should draw the face of the mask closer to the child's face, further minimizing dead space and enhancing the seal of the mask on the child's face.

The soother device orifice may further be situated in a pliable and flexible accordion region 50 of the mask. The purpose of this flexible region is to allow a soother device inserted into the orifice to float slightly, so the soother device can be positioned comfortable in the mouth of the child. The device should be able to move approximately 5 mm up or down (i.e., closer or farther from the nose) without seriously deforming the main body of the mask which could cause a breach in the seal of lip 60 around the face of the patient.

In an embodiment, the flexible accordion region 50 is a bellows-shaped region of the mask (when viewed in cross section). The flexible accordion region 50 may be thinner than the main body of the mask. The thin section and the bellow shape give this area its flexibility.

In an embodiment, the mask may include a breakable or cuttable section that is sealed as packaged for the user, but can be broken or cut by a caregiver to insert a soother device. If this breakable section is not cut, there is no soother device orifice in the mask. If it is cut or broken, an orifice for a soother device is created.

In an alternative embodiment, shown in FIG. 4, the mask may lack a soother device orifice, yet still have the anthropometrically designed ergonomically contoured shape characteristic of the inventive masks.

In an embodiment, the masks may have a combined visual seal indicator and exhalation valve 30 to assist a caregiver monitoring the quality of the seal. The seal indicator may have a plastic or elastomer flap 32 (shown in FIG. 5) that moves from a first position to a second position in response to an inhalation or exhalation. The indicator apparatus is configured so this movement is readily apparent, for example by the use of different colors on either side of flap 32. In an embodiment, the flap is in a first resting position that is also the position during inhalation. During exhalation, the flap moves to a second open position (displaying, for example a different color to an observer) during exhalation as air is exhaled from the mask. The movement of the flap is also critically dependent on the quality of the seal of the mask on the face of the patient. If the mask is poorly sealed, the flap won't move and the caretaker or patient will know that there is a leak around the edge of the mask. Thus, the purpose of the visual seal indicator is primarily to indicate a secured seal, showing that the seal is effective at preventing leakage of air around the edge of the mask.

In an embodiment, the visual seal indicator is a discrete component that fits into an opening on the top of the mask, near the nostrils of the patient. The indicator may have a rigid plastic frame with a movable indicator flap. In an embodiment, the flap may be configured to open away from the face of the user, so that any exhaled active drug is vented in a direction away the face and eyes of the patient.

In an embodiment, a method of administering an inhaled medication to a patient, in particular an aerosolized medication, is provided wherein the inventive mask is placed over the mouth and nose of a patient. In an embodiment, the patient may be from age birth to about five years old. In an embodiment, the patient may be over the age of five years. In an embodiment, the patient is age birth to about five years and the mask has a soother device orifice and the method includes administering an inhaled medication to a child while the child is sucking on a soother device. In an embodiment, the patient is age birth to about five years and the mask has a soother device orifice and the method includes administering an inhaled medication to a child while no soother device is employed.

The size of the mask is selected from the group of dimensions comprising about 59 mm wide and about 64 mm high; about 71 mm wide and about 76 mm high; and about 82 mm wide and about 87 mm high.

The invention claimed is:

1. A method comprising, administering an inhalable medicament to a patient using a pediatric mask, wherein said mask comprises:
a flexible body comprising a nose section and a mouth section, the nose section comprising an opening for receiving said inhalable medication located at the uppermost portion of the nose section and configured to be aligned with the nostrils of said patient; and wherein, the interior surface of said mask is contoured to conform to the profile of said patient to minimize the dead space in said mask.

2. The method of claim 1, wherein said patient has an age between newborn and five years old.

3. The method of claim 1, wherein said mask has a size of about 59 mm wide and about 64 mm high.

4. The method of claim 1, wherein said mask has a size of about 71 mm wide and about 76 mm high.

5. The method of claim 1, wherein said mask has a size of about 82 mm wide and about 87 mm high.

6. The method of claim 1, wherein said mask is a unitary molded plastic article.

7. The method of claim 1, wherein said mask comprises a single opening for receiving said inhalable medication.

8. The method of claim 1, wherein said mask further comprises an exhalation valve on the top of said mask.

9. The method of claim 8, wherein said exhalation valve comprises a flow indicator mounted adjacent to the nostrils of the patient, wherein the flow indicator is configured to move in response to exhalation by the patient thereby providing a visual indication of the quality of the seal around the face of the patient.

10. The method of claim 9, wherein said visual indicator is a colored flap that moves in response to the breathing of the patient during a secured seal.

11. The method of claim 1, wherein the flexible body comprises an edge, said edge comprises a flexible lip angled outward from the interior of said mask.

12. The method of claim 1, wherein the flexible body comprises an edge, wherein said edge is thinner than the flexible body of said mask.

13. The method of claim 11, wherein said flexible lip is composed of an elastomeric material.

14. The method of claim 11, wherein said flexible lip is composed of a pliable plastic silicone.

15. The method of claim 1, wherein said mask is configured to cover said patient's cheeks and fit over said patient's chin.

16. The method of claim 1, wherein an inside dimension height of said mask is 45 mm high to 64 mm high.

17. The method of claim 1, wherein an inside dimension height of said mask is 45 mm high.

18. The method of claim 1, wherein an inside dimension height of said mask is 55 mm high.

19. The method of claim 1, wherein an inside dimension height of said mask is 64 mm high.

20. The method of claim 1, wherein the flexible body is molded.

21. The method of claim 1, wherein the flexible body is elastomeric.

22. The method of claim 1, where the inhalable medication is a gas, a vapor, a mist, an aerosol, or a suspended powder.

23. A method comprising, administering an inhalable medicament to a patient of age birth to about five years using a pediatric mask, wherein said mask comprises:
a flexible body comprising a nose section and a mouth section, the nose section comprising an opening for receiving said inhalable medication located at the uppermost portion of the nose section and configured to be aligned with the nostrils of said patient; and wherein, the interior surface of said mask is contoured to conform to the profile of said patient to minimize the dead space in said mask.

24. A method comprising, administering an inhalable medicament to a person of age birth to five years using a pediatric mask, wherein said mask comprises:
a flexible body comprising a nose section and a mouth section, the nose section comprising an opening for receiving said inhalable medication located at the uppermost portion of the nose section and configured to be aligned with the nostrils of said patient; wherein, the interior surface of said mask is contoured to conform to the profile of said patient to minimize the dead space in said mask; and an orifice in the mouth section configured to insert a soother device there within, wherein a soother device is used.

25. The method of claim 24, wherein the orifice is a duck bill type orifice within a flexible accordion section.

26. The method of claim 24, wherein the orifice is a modified duck bill configured to seal the orifice to prevent leakage of air during inhalation or exhalation when the soother device is inserted into the orifice.

\* \* \* \* \*